United States Patent [19]
Kim et al.

[11] Patent Number: 4,865,773
[45] Date of Patent: Sep. 12, 1989

[54] COLLOID-ACTIVE SYNTHETIC DETERGENT AND PROCESS FOR ITS MANUFACTURE

[76] Inventors: In Kim; Seo Kim, both of 354-7 Myunmok-Dong, Dongdaemoon-Ku, Seoul, Rep. of Korea

[21] Appl. No.: 228,688

[22] Filed: Aug. 5, 1988

Related U.S. Application Data

[63] Continuation-in-part of Ser. No. 24,168, Mar. 10, 1987, abandoned.

[30] Foreign Application Priority Data

May 21, 1986 [KR] Rep. of Korea ................ 3970/1986

[51] Int. Cl.$^4$ ........................ C07C 51/54; C07C 51/56
[52] U.S. Cl. .................................... 252/548; 252/174; 252/174.21; 252/174.22
[58] Field of Search ...................... 252/174.21, 174.22, 252/548, 174

[56] References Cited

U.S. PATENT DOCUMENTS

| | | | |
|---|---|---|---|
| 3,239,468 | 3/1966 | Herrick | 252/152 |
| 3,953,382 | 4/1976 | Nelson | 252/548 |
| 4,016,040 | 4/1977 | Win | 195/68 |
| 4,379,080 | 4/1983 | Murphy | 252/526 |
| 4,613,448 | 9/1986 | Cheng | 252/157 |

OTHER PUBLICATIONS

Schick; Martin J., *Nomonic Surfactants,* N.Y., Marcel Dekker, Inc., 1967, p. 50.
Schöfeldt; N., *Surface Actno Ethylene Oxide Adducts,* N.Y., Pergamon Press, 1969, p. 86.

*Primary Examiner*—John F. Niebling
*Assistant Examiner*—Isabelle Rodriquez
*Attorney, Agent, or Firm*—Birch, Stewart, Kolasch & Birch

[57] ABSTRACT

A novel colloid-active synthetic detergent composition containing microspheres which comprises an alkanol amide prepared by the condensation of a coconut fatty acid with an alkanol amine, isooctylphenoxypolyoxyethylene ethanol, p-tert-octylphenoxypolyethoxy ethanol and ethylene diamine tetraacetic acid, and a process for its manufacture.

6 Claims, No Drawings

COLLOID-ACTIVE SYNTHETIC DETERGENT AND PROCESS FOR ITS MANUFACTURE

CROSS-REFERENCE TO RELATED APPLICATION

This is a continuation-in-part application of U.S. patent application, Ser. No. 07/124,168, filed on Mar. 10, 1987, now abandoned.

BACKGROUND OF THE INVENTION

The present invention relates to a colloid-active synthetic detergent and a process for its manufacture, and more particularly to a novel synthetic detergent such as alkaline nonionic colloidal detergent and a method for producing such a detergent.

There are many types of known synthetic detergents derived from propylene tetramer derivatives such as polypropylene benzenesulfonate-type hard compounds. However, such compounds have some serious ecologic problems such as water contamination and the toxic effect to human body, etc.

Recently, improvements have been made in such detergent for eliminating or resolving these problems. That is, linear benzenesulfonate-type soft synthetic detergents have been developed and widely used instead of the conventional hard detergents. While the soft synthetic detergents have a high degree of decomposability in water, their toxicities are still strong and unacceptable. In some such soft detergents, their toxicities are greater than that of the conventional hard detergents. Accordingly, the use of such soft detergents cannot substantially eliminate the damages to underwater ecologic groups due to the slow release of their toxicity in rivers and waterways. Furthermore, the conventional sulfate-type and sulfonate-type detergents by themselves do not show an adequate effect in detergent mechanism, and thus the use of several additives such as collecting agents, precipitators and chelating agent must accompany the test detergents in practical cleaning processes. Also, the addition of such undesirable additive compounds as submicron calcium carbonate, nitrilotriacetic acid (NTA), hexamethylene diamine tetraacetic acid (HEDTA) and diethylene triamine pentaacetic acid (DTPA) which should be removed during the washing process, has caused eutrophication, damage to skin, degradation of the self-purification ability of water, and may be the reason for the problems of circumference contamination and health preservation.

Several types of detergents containing nonionic surface active agents and having relatively high ecological safety, including Zeolite, have been developed. However, these detergents also have potential problems of health preservation pollution and water contamination.

OBJECTS AND SUMMARY OF THE INVENTION

Accordingly, it is an object of the present invention to provide a novel synthetic detergent such as an alkaline nonionic colloidal composition.

It is another object of the present invention to provide a novel synthetic detergent which is safe to the human body and underwater ecologic groups and can reduce the problems of water contamination, etc.

It is a further object of the present invention to provide an improved synthetic detergent which contains colloidal microspheres of an average particle size of from $10^{-5}$ to $10^{-7}$ cm and is a composition containing a compound prepared by the condensation of a natural vegetable fatty acid with an alkanol amine, a nonionic surfactant having alcohol groups which are partially esterified with a fatty acid, and a polyoxy alcohol, so that it exhibits surprisingly desirable effects as a detergent mechanism.

It is still another object of the present invention to provide an improved detergent which is a strong surface-active agent without ionization which rapidly diffuses into the detergent solution and continues random movements of colloid particles to promote complex activities of the detergent components such as its magnetic property, electrophoresis and its adsorption property, etc. Thus the detergent of the present invention exhibits a unique satisfactory detergent mechanism, and is highly activated in function such as collectivity, surface activity and hyperwetting to perform a superior detergent operation such as penetration, emulsification, diffusion, cleaning, etc., in practical use.

The present invention relates to a novel colloid-active synthetic detergent comprising a composition of a compound prepared by the condensation of a coconut fatty acid with an alkanol amine, isooctylphenoxypolyoxyethoxy ethanol p-tert-octylphenoxypolyethoxy ethanol and ethylene diamine tetraacetic acid and the process for its manufacture.

DESCRIPTION OF PREFERRED EMBODIMENTS

Referring now in detail to the present invention, there is provided a novel colloid-active synthetic detergent containing colloidal microspheres and also having an average particle size of from $10^{-5}$ to $10^{-7}$ cm, said detergent comprising a composition of a compound prepared by the condensation of a coconut fatty acid (saponification value: 271, acid value: 269) with an alkanol amine [$HOCH_2CH_2NH_2$], isooctylphenoxypolyxyethylene ethanol [$(CH_3)_3CCH_2C(CH_3)_2C_6H_4O(CH_2)_2O(C_2H_4O)_7C_2H_4OH$] which is a nonionic type surfactant and p-tert-octylphenoxypolyethoxy ethanol [$(CH_3)_3CCH_2C(CH_3)_2C_6H_4O(CH_2CH_2O)_xH$] (see The Condensed Chemical Dictionary, 8th edition, Gessner G. Wawley, page 484 and 640). In practical use, the detergent of the present invention should be utilized in sufficient water to advantageously promote the detergent mechanism.

In another aspect of the present invention, there is provided a process for producing a novel colloid-active synthetic detergent which comprises the steps of; (a) forming a homogeneous mixture of a compound prepared by the condensation of coconut fatty acid with alkanol amine, iscoctylphenoxypolyoxyethylene ethanol which is a nonionic type surfactant and p-tert-octylphenoxypolyethoxy ethanol, (b) pulverizing the initial mixture by a colloidal process utilizing a milling apparatus, (c) forming hollow microspheres in a spray drying system, (d) screening the microspheres to refine colloidal particles having an average particle size of from $10^{-5}$ to $10^{-7}$ cm, and (e) adjusting the water content and pH in the resulting product.

In a preferred embodiment of the present invention, the colloid-active synthetic detergent comprises about from 20 to 25 parts by weight of all the compound prepared by the condensation of the coconut fatty acid with the alkanol amine, from 18 to 22 parts by weight of isooctylphenoxypolyoxyethylene ethanol-type nonionic surfactant from 12 to 15 parts by weight of p-tert-octyl-phenoxypolyethoxy ethanol, from 42 to 45 parts by weight of water, and about 1 part by weight of ethylene diamine tetraacetic acid as an additive.

The condensation of the coconut fatty acid with the alkanol amine may be accomplished by heating a mixture of the reactants at about 150° C. The resultant product can be separated and purified by the conventional techniques well-known in the art. In this case, when an alkaline-type detergent is desired, the pH of the product may be adjusted to about 10 by adding monoethanol amine. On the contrary, in this case when an acidic detergent is desired, the pH of the product may be adjusted to about 4 by adding citric acid.

When the detergent of the present invention is dispersed in water, the detergent forms colloidal dispersant as micelles, and such colloidal particles produce a complicated collision effect with surface-charged particles through mutual random reactions.

As a result, the colloidal particles directly penetrate into the contaminants and vigorously agitate oils, grease, dust and soil in the contaminants for separating and floating them from the articles to be cleaned. Such a deterging mechanism of the present invention performs such a continuous as highly action so that is expected to achieve superior function to that of conventional detergents. This improvement in the detergent mechanism is a functional characteristic of the colloid-active detergent of the present invention.

In practice, water is the important factor to functionalize the characteristic deterging mechanism. In a preferred embodiment of the present invention, water is present in amount of from about 42 to 45 percent by weight. The deterging ability of the colloid-active detergent of the present invention is substantially constant whether it is functionalized with hard water or soft water, or fresh water or salt water.

The colloidal-active synthetic detergent of the present invention does not contain the conventional pollution-inductive toxic materials such as phosphates, nitrates and nitrilotriacetic acid, etc. In addition, since the detergent has the function to separate hard mineral ions of water in the detergent solution, it does not form any hard water-reacting precipitates in hard water medium and thus stabilizes the surface activity of the surfactant component.

The colloid-active detergent of the present invention has a very high degree of microbial decomposability, and thus it may be substantially decomposed within a short period in the sea or rivers. Furthermore, the detergent of the present invention may be easily decomposed by microorganisms even at relatively low temperature. It is determined that the degree of microbial decomposability of the detergent sol in water at 25° C. is about 90% after 24 hours and 99.93% by weight after seven days. This means that environmental pollution of the detergent of the present invention may be disregarded when compared to the conventional detergents.

It is expected that by utilizing the colloid-active synthetic detergent of the present invention, the discharge of contaminated water containing undesirable toxic organic compounds, and the adverse effect on underwater ecologic groups and environmental pollution can be eliminated or minimized since the detergent has characteristics in deterging mechanism to activate the inherent nature of the colloidal particles at low concentration to perform very excellent complex deterging functions and does not contain considerable amounts of unacceptable additives. It is also expected that the colloid-active detergent of the present invention can be widely used in a wide scope of general or special industrial applications since the detergent can be used with both acid and alkaline base.

The lyophobic colloid in the detergent solution of the present invention consists of a long hydrocarbon tail and a polar head group. This is called as micelle. As the concentration of solution increases, the micelles form crystalline assemblies. In this case, the hydrocarbon tails are placed toward the inside of the micelle assemblies and the polar head groups are contacted with water molecules. The formation of the micelle assemblies increases within an increase in the interaction between the hydrocarbon tails groups and the replacement of the circumference of hydrophobic groups with hydrophilic groups. The head groups interfere with each other by charge repulsion of the polar groups gathering around the micelle surfaces. As the length of the tails of the hydrocarbon groups increase, the interaction of the tails also increases. As the concentration of salts in the detergent solution is higher, the repulsion of the head groups is smaller since their charges are protected by ions of the salts.

Typically, a micelle of the colloid-active detergent contains about fifty soap molecules. Accordingly, the micelles can capture and dissolve relatively water-insoluble contaminants. In practice, it has been proved that insoluble waxes, complex alcohols, oil-based dyestuffs and other materials in dilute solutions of the conventional synthetic detergents can be dissolved in the dilute washing solution of the colloid-active detergent sol of the present invention.

It is presumed that, in the lyophobic sol of the colloid-active synthetic detergent of the present invention, the diffused particles may form two phases irreversibly associated according to the following second-order reaction rate rule.

$$\frac{Co}{C} - 1 = KCoT$$

wherein,

C is the number of particles per cc at time T,

Co is the number of particles at the initial time, and

K is the Boltzmann's constant.

In the above equation, in case of KCoT-1, the value of Co at the initial time is ½. As the time T increases, the values of K and Co become smaller. The concentration of the initial sol, half-value period which is 1 minute at 25° C. (room temperature), is about $1.4\times10^9$ particles/cc in solution on condition of no interference to association. The average particle size of the colloids is about $10^{-6}$ cm and the volume fraction of the particles in the sol is about 0.07. The particles are electrically charged in the sol and their electric charges appear through electrophoresis. It has been determined that the surface tension of tap water decreases by one-half by the simple addition of the colloid-active synthetic detergent of the present invention at a concentration less than 1/3250.

The following examples illustrates the present invention but they are not intended to limit the scope of the invention in any way. All parts and percentages are by weight unless otherwise indicated.

EXAMPLE 1

Preparation of Colloidal-Active Synthetic Detergent

To 22.5 parts by weight of alkanol amide, which is prepared by the condensation of a coconut fatty acid (14 moles, saponification value: 272, acid value: 269) with an alkanol amine (3.0 moles, $HOCH_2CH_2NH_2$) at 150° C., is added 20 parts by weight of isooctylphenoxypolyoxyethylene ethanol-type nonionic surfactant and 43 parts by weight of distilled water. The mixture is slowly heated to 70° C. with stirring to form an initial mixture. To the initial mixture, 13.5 parts by weight of p-tert-octylphenoxypolyphenoxy ethanol and 1 part by weight of ethylene diamine tetraacetic acid are added to form a free-flowing liquid slurry. The liquid slurry is stirred for 60 minutes and then is introduced into a drop tank.

In the drop tank, the liquid slurry is filtered through a refine filter disposed in the middle of the tank and the unreacted materials are removed from the mixture. Thereafter, the refined slurry is introduced into a cylindrical chamber-type spray drier through a spray nozzle. In the cylindrical chamber, the liquid slurry from the nozzle is contacted with hot air at a temperature of about 150° to 200° C. through a valve adjoined to the chamber, to form as a colloidal microsphere product. The microspheres of the product are further pulverized at 70° to 140° C. in a milling apparatus so that the density is above 25 $lb/ft^3$. The surfaces of the microspheres are finished in a drum apparatus and about 18% by weight of water content of the particles is reduced.

The resultant microspheres are passed through a fine screening apparatus ( −14 to +65 mesh, Tyler Screen Size ) under pressure and refined as colloidal particles having an average particle size of from $10^{-5}$ to $10^{-7}$ cm. Then, the water content of the colloidal particles is reduced about 20% by weight to have density of from 40 to 46 $lb/ft^3$. The final products comprise colloidal particles in the form of hollow microspheres having an average particle size of from $10^{-5}$ to $10^{-7}$ cm. The H.L.B. of the products is about 14.8.

The physical properties of the colloidal-active detergent of the present invention are listed below:

pH: 10.4+0.1 (adjusted by monoethanol amine)
Boiling Point: 93° C.
Vapor pressure: 17.0 mmHg
Specific Gravity: 1.017 +0.01 (20°)
Conductivity: 0.036 mhos/cm
Evaporation Rate: 0.7 of Butyl Acetate
Surface Tension: 29.5 dynes/cm
Viscosity: 110±5 centipoise (20° C.)
Solubility in Water: E (excellent)

EXAMPLE 2

The safety of the synthetic detergent prepared in the Example 1 is evaluated. A test for damage to skin, a test for stimulus to eye, and a test for toxicity of oral administration is employed.

(1) Test for Damage to Skin

For the test, optionally selected six white Albino rabbits (weight: 2.5–3.0 Kg, place of the origin: New Zealand) are used.

The skins of the Albino rabbits are treated with the synthetic detergent of Example 1 and are covered with gauzes (1 inch×1 inch). In the test, partial portions of three Albino rabbits (No. 1, 3 and 50 are slightly injured before applying the detergent. However, the skins of rest three Albino rabbits (No. 2, 4 and 6) are not injured before applying the detergent. After applying the detergent to the skins of the Albino rabbits, observation are taken at 24, 48, 72, 360 and 720 hours of lapsed time. The results are give in Table I.

TABLE I

| | 24 hrs | | 48 hrs | | 72 hrs | | 360 hrs | | 720 hrs | |
|---|---|---|---|---|---|---|---|---|---|---|
| Albino rabbits | A RS | N RS | A RS | N RS | A RS | N RS | A RS | N RS | A RS | N RS |
| No. 1 | 10 | 00 | 00 | 00 | 00 | 00 | 00 | 00 | 00 | 00 |
| No. 2 | 00 | 00 | 00 | 00 | 00 | 00 | 00 | 00 | 00 | 00 |
| No. 3 | 10 | 00 | 00 | 00 | 00 | 00 | 00 | 00 | 00 | 00 |
| No. 4 | 00 | 00 | 00 | 00 | 00 | 00 | 00 | 00 | 00 | 00 |
| No. 5 | 10 | 00 | 00 | 00 | 00 | 00 | 00 | 00 | 00 | 00 |
| No. 6 | 00 | 00 | 00 | 00 | 00 | 00 | 00 | 00 | 00 | 00 |

In the Table I, the following abbreviations are defined as follows:

A : damaged portions (injured portions)
N : normal portions
R : measles
S : water blister The skins of three Albino rabbits (No. 4, 4 and 6), which are not injured before the test, are not damaged by contact with the detergent of Example 1.

(2) Test for Stimulus to Eve

For the test, nine, randomly selected white Albino rabbits (weight: 2.3–2.8 kg) are used. The nine rabbits are divided into three groups (A, B and C).

For each group, 0.1 ml of the detergent of Example 1 is applied to left-side eye of each rabbit under the following conditions:

Group A: The eye is washed with water immediately after application of the detergent.
Group B: The eye is washed with water five seconds after application of the detergent.
Group C: The eye is not washed after application of detergent.

In the meantime, the right-side eye of each rabbit is not treated with the detergent of Example 1 for comparison. Observation is taken at 24, 48 and 72 hours of lapsed time. The results are given in Table II.

TABLE II

| Albino rabbits | 24 hours | | | 48 hours | | | 72 hours | | |
|---|---|---|---|---|---|---|---|---|---|
| Group No. | Cor | Iri | Conj | Cor | Iri | Conj | Cor | Iri | Conj |
| A-1 | op-0 | 0 | c-0<br>r-0<br>d-0 | op-0 | 0 | c-0<br>r-0<br>d-0 | op-0 | 0 | c-0<br>r-0<br>d-0 |
| A-2 | op-0 | 0 | c-0<br>r-0<br>d-0 | op-0 | 0 | c-0<br>r-0<br>d-0 | op-0 | 0 | c-0<br>r-0<br>d-0 |
| A-3 | op-0 | 0 | c-0<br>r-0<br>d-0 | op-0 | 0 | c-0<br>r-0<br>d-0 | op-0 | 0 | c-0<br>r-0<br>d-0 |
| B-1 | op-0 | 0 | c-1<br>r-1<br>d-0 | op-0 | 0 | c-0<br>r-0<br>d-0 | op-0 | 0 | c-0<br>r-0<br>d-0 |
| B-2 | op-0 | 0 | c-0<br>r-0<br>d-0 | op-0 | 0 | c-0<br>r-0<br>d-0 | op-0 | 0 | c-0<br>r-0<br>d-0 |
| B-3 | op-0 | 0 | c-0<br>r-0<br>d-1 | op-0 | 0 | c-0<br>r-0<br>d-0 | op-0 | 0 | c-0<br>r-0<br>d-0 |
| C-1 | op-1 | 0 | c-0<br>r-0<br>d-1 | op-0 | 0 | c-0<br>r-0<br>d-0 | op-0 | 0 | c-0<br>r-0<br>d-0 |
| C-2 | op-0 | 0 | c-0<br>r-1<br>d-0 | op-0 | 0 | c-0<br>r-0<br>d-0 | op-0 | 0 | c-0<br>r-0<br>d-0 |

TABLE II-continued

| Albino rabbits Group No. | 24 hours Cor | Iri | Conj | 48 hours Cor | Iri | Conj | 72 hours Cor | Iri | Conj |
|---|---|---|---|---|---|---|---|---|---|
| C-3 | op-0 | 0 | c-0 r-1 d-0 | op-0 | 0 | c-0 r-0 d-0 | op-0 | 0 | c-0 r-0 d-0 |

In the Table II, the abbreviations are defined as follows:

Cor: Cornea, op - opaque (level: 0–4)
Iri: Iris, level: 0–2
Conj Conjunctiva,
c- camosis (level: 0–4)
r- hyperemia (level: 0–3)
d- mucous discharge (0–3)

Explanations

Group A: Stimulus to eye is not observed.

Group B: No substantial change (effect) is not observed in cornea. Slight changes are observed in conjunctiva of two rabbits among three, but the effect disappears after 72 hours.

Group C: Slight change is observed in cornea of one rabbit and in conjunctivas of three rabbits, but the changes nearly disappears after 48 hours and completely disappears after 72 hours.

(3) Test for Toxicity of Oral Administration

For the test, eighty white Albino rabbits (weight: 2.5–3.2 Kg) is used. Among the eighty rabbits, forty are male and forty are female. The rabbits are divided into four groups. Each group consists of ten male rabbits and ten female rabbits.

Before carrying out the test, all rabbits are not fed with food for 24 hours. Then, the detergent of Example 1 is fed to each rabbits by oral administration. Observations are taken everyday for two week period. The results are given in Table III.

TABLE III

| Group No. | Dosage of Detergent (mg/Kg of weight) | Number of Survival after two weeks Male | Female |
|---|---|---|---|
| 1 | 3.0 mg/Kg | 10/10 | 10/10 |
| 2 | 6.0 mg/Kg | 10/10 | 10/10 |
| 3 | 9.0 mg/Kg | 10/10 | 10/10 |
| 4 | 12.0 mg/Kg | 10/10 | 10/10 |

The results indicate that the oral administration of the present detergent does not exhibit significant toxic effect to Albino rabbits. From these results, it can be expected that the detergent also will not show significant toxic effects to the human body or other mammals.

EXAMPLE 3

Test for Toxicity to Waterfowls

The effect of the detergent of Example 1 to Waterfowls is evaluated by a test of toxicity. The test is carried out by an oral administration method described below.

For the test, ten randomly selected drakes (Mallard-hybrid, weight: 1.5–2.0 Kg) are used as the test Group 1. To each drake, about 15 ml of the detergent is fed by oral administration through a tube. After oral application, drakes are maintained in a cage (1 ft×12×8 ft) provided with feed cups and water cups. In the meantime, the test is applied to two other drakes (Comparison group 1) in the same manner except that the cage is provided with only water cups. The effect of the detergent on drakes data of survival are given in Table III -1 and the states of the drakes are set forth below.

For the test, ten drakes (Mallard-hybrid, weight: 1.5–2.0 Kg) are used as test Group 1. To each drake, about 15 ml of the detergent is fed by oral administration through tube. After oral application, drakes are maintained in a cage (1 ft×12 ft×8 ft ) providing with feed cups and water cups. In the meantime, the test is applied to the other two drakes (Comparison group 1) in the same manner except that the cage is provided with only water cups. The effect of the detergent on drakes is observed over a 48 hour period. The results of the survival data are given in Table III -1 and the states of the drakes are set forth below.

TABLE III - 1

| Drakes | Number of Survival after 24 hours | after 36 hours | after 48 hours |
|---|---|---|---|
| Group 1 | 10/10 | 10/10 | 10/10 |
| Comparison Group 1 | 2/2 | 2/2 | 2/2 |

All the drakes vomited a portion of the detergent applied by oral administration within 20 minutes. The amount of the detergent vomited is about 25–30% of the total dosage for each drakes. However, about 1 hour after oral administration, feed and water was provided in the cage and all actions were normal actions.

The above-mentioned testes are repeated with the ten drakes (Group 2) and two drakes (Comparison Group 2) except that 15 ml of the detergent-water ( 1 : 40 ) solution is applied to each drake by oral administration instead of 15 ml of the detergent. The effect on drakes is also observed over a 48 hour period. The results for data of survival is given in Table III -2 and the states of the drakes are set forth below.

TABLE III - 2

| Drakes | Number of Survival after 24 hours | after 36 hours | after 48 hours |
|---|---|---|---|
| Group 2 | 10/10 | 10/10 | 10/10 |
| Comparison Group 2 | 2/2 | 2/2 | 2/2 |

All the drakes did not vomit the detergent-water solution applied by oral administration. They stood silent for about ten minutes, and then shows normal actions by taking feed.

In addition, the further observation for effect of the detergent of Example 1 on the drakes is carried out. From each group (Group 1 and 2, Comparison Group 1 and 2), one drake is optionally selected. The four drakes are anatomized and their internal vital organs are visually observed. Any significant changes and damages are not observed on their internal vital organs. This indicates that the detergent of Example 1 does not have oral toxicity to waterfowls.

EXAMPLE 4

The safety of the detergent of Example 1 to underwater ecologic groups is evaluated.

(1) Test of Safety to Microorganisms

To 100 g of the detergent of Example 1,300 g of water is added to prepare a concentrated detergent solution. Five cuts of conc. detergent solution are used for the test. To the five cuts of the detergent solution, different amounts of salt water is individually added to form five standard solutions. Thirty Artemia Sallina nauplii are put into 150 ml of each standard solution. In the meantime, the other 30 Artemia Sallina nauplii are put into 150 ml of sea water for comparison. The standard solutions and the control solution (sea water) are maintained at 20° C. through the test. Observations are taken over a 48 hour period. The results for data of survival are given in Table IV -1.

TABLE IV - 1

| Test Solution | | Number of Survival | |
|---|---|---|---|
| Standard Sol. No. | Concentration | after 24 hours | after 48 hours |
| 1 | 0.739 mg/l | 28/30 | 28/30 |
| 2 | 0.554 mg/l | 30/30 | 29/30 |
| 3 | 0.416 mg/l | 29/30 | 28/30 |
| 4 | 0.312 mg/l | 30/30 | 30/30 |
| 5 | 0.231 mg/l | 30/30 | 30/30 |
| control | — | 30/30 | 30/30 |

The above tests are repeated using five fresh sets of standard solutions and one control under the same conditions. The same results are obtained. This example illustrates that the detergent of the present invention is safe to the under waterfowls.

(2) Test of Safety to Seafishes

The concentrated detergent solution is prepared by adding 300 g of water to 100 g of the synthetic detergent of Example 1. Five cuts of the concentrated detergent solution are used for the tests. To the five cuts of the detergent solutions, different amount of seawater is individually added to form five various sets of standard solutions. Sixty stickleback are put into each standard solutions. Sixty stickleback are put into each standard solution contained in a separated aquarium. In addition, as control, sixty sticklebacks are put into an aquarium containing natural seawater. Observations are taken over a 72 hour period. The results for data of survival at 24, 48 and 72 hours of lapsed time are given in Table IV -2.

TABLE IV - 2

| Test Solution | | Number of Survival | | |
|---|---|---|---|---|
| Standard Sol. No. | Concentration | after 24 hours | after 48 hours | after 72 hours |
| 1 | 0.739 mg/l | 20/60 | 19/60 | 17/60 |
| 2 | 0.554 mg/l | 22/60 | 22/60 | 19/60 |
| 3 | 0.416 mg/l | 31/36 | 28/60 | 25/60 |
| 4 | 0.312 mg/l | 33/60 | 30/60 | 28/60 |
| 5 | 0.231 mg/l | 35/60 | 32/60 | 30/60 |
| control | — | 49/60 | 48/60 | 48/60 |

After 96 hours, the survived sticklebacks are moved to fresh seawater. They survived for several days except two died during movement.

(3) Test for Safety to Goldfishes

To 100 g of the detergent of Example 1, 300 g of fresh water is added to prepared concentrated detergent solution. Five cuts of the concentrated detergent solution are used for the tests. Five standard solutions are also prepared as the above-mentioned tests. Sixty Golden Shiners are applied for each standard solution. Observations are taken over a 72 hour periods. The results for survival at 24, 48 and 72 hours of lapsed time are given in Table IV-3.

TABLE IV - 3

| Test Solution | | Number of Survival | | |
|---|---|---|---|---|
| Standard Sol. No. | Concentration | after 24 hours | after 48 hours | after 72 hours |
| 1 | 0.739 mg/l | 29/60 | 27/60 | 24/60 |
| 2 | 0.554 mg/l | 32/60 | 29/60 | 29/60 |
| 3 | 0.416 mg/l | 35/60 | 32/60 | 31/60 |
| 4 | 0.312 mg/l | 60/60 | 60/60 | 58/60 |
| 5 | 0.231 mg/l | 60/60 | 60/60 | 60/60 |

EXAMPLE 5

The practical applicabilities and effect of the synthetic detergent of Example 1 under conditions required for the washing and refining of fibers articles are evaluated. The synthetic detergent of Example 1 is alkaline colloidal compositions having a pH of 10.2 to 10.4 at normal concentration. A 1-2% aqueous solution of the colloidal detergent shows a weak alkaline solution having pH of from 8.2 to 8.5. The colloidal detergent of Example 1 does not react with $H^+$ ion or $OH^-$ ion of water and thus does not form any weak acidic salts or basic salts.

In practical application, the detergent of Example 1 exhibits good or excellent cleaning effect for fiber articles. More particularly, a 1-2% aqueous solution of the present detergent, with a pH of below 8.5, shows very good detergent functions for cottons, wools, nylons and polyesters without causing damage and abrasion.

(1) cotton - Cellulose ($C_6H_{10}O_5$)

Specific Gravity: 1. 54
Wettability: 7.0-8.5%
Tensile Strength: 60 psi

Several cotton fabrics are cleaned with 0.3% aqueous solution of the detergent of Example 1. There are no adverse effects to the fabrics. In case of refining, there are not any changes on the characteristics of the cotton fiber. After rinsing with water, the cotton fabrics shows prominent difference in luminescence phenomenon and color appearance.

(2) Woolen Fabrics

Specific Gravity: 1.32
Wettability: 11-17%
Tensile Strength: 17-29×$10_3$ psi

Woolen fabrics are spoiled by hot concentrated sulfuric acid, but are resistant to weak acids. It has been found that woolen fabrics can be cleaned without damages by simple washing and rinsing wit 0.7-0.9% aqueous solution of the present colloidal detergent.

In the process of cleaning, the optimum pH of the cleaning solution to separate waxes in the wool is about 10 while the optimum pH to float the soils is about 7.0. The processes using conventional synthetic detergent solutions employ Sodium Carbonate to adjust the pH of the cleaning solution. Thus, the detergent ability must be reduced and the woolen fabrics may be eroded by alkaline materials as well as requiring separate multiple steps. However, in the case of the process for using the present colloidal-active synthetic detergent, woolen fabrics can be cleaned without employing such separate steps to adjust the pH of solution.

Woolen fabrics are treated with 0.7–0.9% aqueous solutions of the detergent of Example 1 without the additional steps to adjust pH of the solution using Sodium Carbonate, and evaluated for cleanliness. Woolen fabrics are judged to be satisfactorily clean. It is determined that the residual content of waxes was only about 0.50–0.75% and the residual content of active components after rinsing is only about 0.021 ppm. In addition, erosion of fabrics by alkaline material is observed.

The results indicate that a dilute solution of the present detergent having a pH of about 8, can perform its excellent detergent functions without separate steps to adjust pH by addition of Sodium Carbonate and the erosion of fabrics by alkaline materials. It is presumed that such excellent functions may be due to the effect of characteristic colloidal activity of the present detergent.

(3) Nylons (Polyamides)

Nylons have characteristics to be decomposed by concentrated acids. But they are resistant to weak acids. In general, acidic dyes are used in dyeing of Nylon-type fabrics.

Nylon coupons are cleaned with 0.7% aqueous solution of the detergent of Example 1 and evaluated for cleanliness. All coupons are judged to be totally clean. The phenomenon of wire mole, luminescence and color appearance is superior to those cleaned with conventional sulfate-aliphatic alcoholic detergent solutions. In addition, for comparison, Nylon coupons are dyed with some different dyes such as acidic dye, chromic dye, etc. they are cleaned with the aqueous solution of the detergent of Example 1. In all cases, there are no changes in color and quality of the coupons.

(4) Polyester Fabrics

Coupons of polyester fabrics are cleaned with 0.72 percent aqueous solution of the detergent of Example 1 and evaluated for cleanliness. The coupons are judged to be satisfactorily clean without any damages to fiber substrate and color.

(5) Silks

Two groups (1 and 2) of coupons having the same quality are used for the tests. The coupons of group 1 are cleaned with 0.2% aqueous solution of the detergent of Example 1. The coupons of group 2 are cleaned with 0.2% aqueous solution of the conventional alkylsulfate-type synthetic detergent which requires the addition of Sodium Carbonate and/or Sodium Hydrogen Carbonate at a pH of 10. The coupons of group 1 and 2 are evaluated for cleanliness. The coupons of group 1 are more desirably cleaned in comparison with the coupons of group 2. From the results, it is determined that the cleaning solution of the present detergent can perform its characteristic functions without Sodium Carbonate.

EXAMPLE 6

This example illustrates the use of the detergent of Example 1 in the industrial processes for refining waste printed papers.

Waste printed papers are refined using the synthetic detergent of Example 1 in the amount of about 0.33 weight % based on the total weight of the waste papers, at a temperature of about 50° C., without the addition of Sodium Peroxide which is generally added in the conventional drink processes. The fiber pulps are totally refined even without a long period agitation in the digestion tank.

In the conventional processes for refining waste printed papers, addition of additives such as chelating agent and long period of washing procedure should be required to control alkaline reaction or water quality. On the other hand, in the refining process using the present detergent, unexpectedly excellent results could be obtained by simple washing procedure without using additives. Furthermore, treatment of waste water also could be accomplished by simple process.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A colloid-active synthetic detergent composition containing colloidal microspheres disposed therein which comprises:

an alkanol amide prepared by the condensation of a coconut fatty acid with an alkanol amine., isooctylphenoxypolyoxyethylene ethanol, distilled water, p-tert-octylphenoxypolyethoxy ethanol, and ethylene diamine tetraacetic acid, the colloidal microspheres having an average particle size of about $10^{-5}$ cm to $10^{-7}$ cm, wherein the alkanol amide, isooctylphenoxypolyoxyethylene ethanol, distilled water, p-tert-octylphenoxypolyethoxy ethanol, and ethylene diamine tetraacetic acid are present in an amount of about 28–30%, 25–27%, 26–28%, 16–18%, and 1% by weight, respectively.

2. The colloid-active synthetic detergent composition of claim 1, wherein the coconut fatty acid has a saponification value of about 271 and an acid value of 269.

3. A process for preparing a colloid-active synthetic detergent sol composition containing colloidal microspheres disposed therein which comprises the steps of:

(a) forming a liquid slurry mixture by mixing together 20–25 parts by weight of an alkanol amide prepared by condensation of coconut fatty acid with alkanol amine, with 18–22 parts by weight of isooctylphenoxypolyoxyethylene ethanol, 42–45 parts by weight parts of distilled water, 12–15% by weight of p-tert-octylphenoxypolyethoxy ethanol, and 1 part of weight of ethylene diamine tetraacetic acid;

(b) subjecting said initial slurry spray dried with hot air to form a product containing microspheres therein;

(c) pulverizing said microspheres to produce colloidal microspheres; and (d) screening said colloidal microspheres to recover uniformed colloidal microspheres having substantially the same average particle size of from $10^{-5}$ cm to $10^{-7}$ cm.

4. The process of claim 2, wherein the mixture of the step (a) comprises 22.5% by weight of alkanol amide, 20% by weight of iscooctylphenoxypolyoxyethylene ethanol, 43% by weight of distilled water, 13.5% by weight of p-tert-octylphenoxypolyethoxy ethanol, and 1% by weight of ethylene diamine tetraacetic acid.

5. The process of claim 2, wherein the coconut fatty acid has a saponification value of about 271 and an acid value of about 269.

6. A colloid-active synthetic detergent composition produced by the process of claim 1.

* * * * *